US012661233B2

(12) United States Patent
Marnay et al.

(10) Patent No.: US 12,661,233 B2
(45) Date of Patent: Jun. 23, 2026

(54) INTERVERTEBRAL DISK PROSTHESIS

(71) Applicants:Thierry Marnay, Montpellier (FR);
Erick Cloix, Cap Ferret (FR)

(72) Inventors: Thierry Marnay, Montpellier (FR);
Erick Cloix, Cap Ferret (FR)

( * ) Notice: Subject to any disclaimer, the term of this
patent is extended or adjusted under 35
U.S.C. 154(b) by 0 days.

(21) Appl. No.: 18/046,588

(22) Filed: Oct. 14, 2022

(65) Prior Publication Data

US 2024/0122721 A1    Apr. 18, 2024

(51) Int. Cl.
A61F 2/44        (2006.01)
(52) U.S. Cl.
CPC .................................... A61F 2/442 (2013.01)
(58) Field of Classification Search
CPC ........ A61F 2/441; A61F 2/442; A61F 2/4425;
A61F 2002/444; A61F 2/4465
See application file for complete search history.

(56) References Cited

U.S. PATENT DOCUMENTS

| | | | | |
|---|---|---|---|---|
| 4,932,969 A | * | 6/1990 | Frey ......................... | A61F 2/442 |
| | | | | 623/17.12 |
| 6,893,465 B2 | | 5/2005 | Shi | |
| 6,936,070 B1 | | 8/2005 | Muhanna | |
| 8,147,555 B2 | | 4/2012 | Kamran | |
| 8,540,772 B2 | | 9/2013 | Osman | |
| 8,632,592 B2 | | 1/2014 | Barrall | |

| | | | | |
|---|---|---|---|---|
| 10,010,427 B2 | | 7/2018 | Diwan et al. | |
| 2004/0186576 A1 | * | 9/2004 | Biscup .................... | A61F 2/442 |
| | | | | 623/17.14 |
| 2005/0197702 A1 | * | 9/2005 | Coppes ................... | A61F 2/441 |
| | | | | 623/17.13 |

(Continued)

FOREIGN PATENT DOCUMENTS

| | | |
|---|---|---|
| EP | 0277282 A1 | 8/1988 |
| EP | 2967910 B1 | 7/2017 |

(Continued)

OTHER PUBLICATIONS

International Search Report and Written Opinion Of The International Searching Authority in PCT/EP2023/078448, dated Jan. 26, 2024, 19 pages.

*Primary Examiner* — Eduardo C Robert
*Assistant Examiner* — Anna V. Little
(74) *Attorney, Agent, or Firm* — FARBER. LLC

(57)        ABSTRACT
Intervertebral disk prosthesis comprising an external waterproof multilayered deformable casing surrounding a peripheral partition membrane delimiting an outer space and an inner cavity, wherein the inner cavity is partitioned by vertical walls delimiting at least four cavity compartments configured to be filled with a non-toxic saline solution, and wherein the vertical walls comprise orifices and/or porous membranes configured to induce the saline solution to flow from one cavity compartment toward another upon heterogeneous application of a pressure comprised between 0.05 and 3 MPa in a duration comprised between 10 seconds and 60 minutes, and to revert back to its native compartment upon removal of said pressure in a duration comprised between 10 seconds and 180 minutes, and wherein the walls are distributed asymmetrically in the inner cavity so that a posterior part of the inner cavity comprises fewer and/or larger cavity compartments than an anterior part of the inner cavity.

16 Claims, 1 Drawing Sheet

(56)                    References Cited

U.S. PATENT DOCUMENTS

| | | | |
|---|---|---|---|
| 2005/0288678 A1* | 12/2005 | Reiley ....................... A61F 2/28 | |
| | | | 606/93 |
| 2006/0009844 A1 | 1/2006 | Bloemer et al. | |
| 2007/0050032 A1* | 3/2007 | Gittings ............... A61F 2/4425 | |
| | | | 623/17.13 |
| 2007/0150063 A1* | 6/2007 | Ruberte .................. A61F 2/442 | |
| | | | 623/23.76 |
| 2007/0179621 A1* | 8/2007 | McClellan, III ........ A61F 2/442 | |
| | | | 264/241 |
| 2009/0240334 A1* | 9/2009 | Richelsoph ............. A61F 2/441 | |
| | | | 623/17.16 |
| 2010/0100185 A1* | 4/2010 | Trieu .................... A61F 2/4425 | |
| | | | 623/17.11 |
| 2010/0234954 A1 | 9/2010 | Justis et al. | |
| 2010/0256766 A1* | 10/2010 | Hibri .................... A61F 2/4611 | |
| | | | 623/17.16 |
| 2013/0131808 A1 | 5/2013 | Suh et al. | |
| 2015/0073422 A1* | 3/2015 | Chegini ............. A61B 17/8827 | |
| | | | 606/94 |
| 2020/0229937 A1 | 7/2020 | Diwan et al. | |

FOREIGN PATENT DOCUMENTS

| | | | | |
|---|---|---|---|---|
| KR | 20130068860 A | * | 6/2013 | ............... A61F 2/44 |
| WO | 2000069374 A1 | | 11/2000 | |
| WO | 2001049192 A1 | | 7/2001 | |
| WO | 0217825 A2 | | 3/2002 | |
| WO | 2006060482 A2 | | 12/2005 | |
| WO | 2008131498 A1 | | 11/2008 | |
| WO | 2020106350 A2 | | 5/2020 | |

* cited by examiner

INTERVERTEBRAL DISK PROSTHESIS

The present disclosure relates to the field of intervertebral prosthesis. In particular to the field of devices which can be used when intervertebral disks are damaged.

Intervertebral disks, sometimes also referred to as intervertebral fibrocartilage, are structures comprised between adjacent vertebrae which can be deformed when one vertebra moves relatively to another vertebra, thus acting both as a joint and as a shock absorber.

Indeed, depending on the movement intervertebral disks can be submitted to very high pressures, especially in case of subjects that are overweight, as a significant part of the weight can eventually be absorbed by the intervertebral disks.

In order to face such dramatic constraints, intervertebral disks present a central gel-like nucleus and a fibrous outer ring. The nucleus can redistribute the pressure applied to the disk in all directions whereas the fibrous ring can withstand high compressive forces.

When the intervertebral disk is dysfunctional or damaged, e.g. in case of a herniation or complete degeneration, which can be caused by intense and repeated stress of the disk, or by a height loss due to dehydration of the nucleus, a need for prosthesis may arise so as to avoid surgically fusing the vertebrae.

However, due to the high pressures which are to be withstood, mimicking natural structures is not an option. Indeed, without natural regeneration, such structures would not be able to last over time.

Prosthesis also needs to be of low encumbrance. Indeed, due to their size existing prosthesis often need to be set up through the belly, thus requiring two surgeons, one for the guts and one for the spine, making it the surgery very expensive. This is mostly true for the lumbar prosthesis as cervical vertebrae are easier to access.

Existing prosthesis usually makes contact with the vertebrae through a titanium convex shape treated to hang properly with the bones. Over time however, metallic structures tend to form cations which are cancerogenic, making those structures unsuitable.

Therefore, known prosthesis are usually made of a deformable chamber filled with a liquid or a gel which can absorb the pressure applied in case of a deformation. Such prosthesis present several issues. Most importantly, the kinetics to absorb the deformation and to return to its initial shape when the pressure is suppressed is not handled in a satisfying manner. Furthermore, pressure tends to be applied heterogeneously on the disk, and regular prosthesis allow only for an homogeneous response, which can be inadequate and, eventually, damage the vertebrae. Lastly, such prosthesis cannot withstand very high pressure, such as the one caused by subject that are overweight when in a squatting position.

There is thus a need for an intervertebral prosthesis to provide an heterogeneous response to heterogeneous pressure, which can withstand high pressure, and presents a deformation kinetics adapted to physiological conditions.

The present disclosure provides an answer to these needs and relates to an intervertebral disk prosthesis comprising an external waterproof multilayered deformable casing surrounding a peripheral partition membrane delimiting an outer space and an inner cavity, wherein the inner cavity is partitioned by vertical walls delimiting at least four cavity compartments configured to be filled with a non-toxic saline solution, and wherein the vertical walls comprise orifices and/or porous membranes configured to induce the saline solution to flow from one cavity compartment toward another upon heterogeneous application of a pressure. In certain embodiments, the pressure is between 0.05 and 3 MPa. In certain embodiments, the pressure is applied for a duration between 10 seconds and 60 minutes. In certain embodiments, the prosthesis reverts back to its native compartment upon removal of said pressure. In certain embodiments, the reversion is between 10 seconds and 180 minutes. In certain embodiments, the walls are distributed asymmetrically in the inner cavity so that a posterior part of the inner cavity comprises fewer and/or larger cavity compartments than an anterior part of the inner cavity.

Waterproof is to be understood as able to contain the fluids which are to be in contact with the casing in the conditions in which the prosthesis is to be used, especially under high pressure. Indeed, it is of utmost importance to prevent leakage which would ruin the properties of the device.

Deformable is to be understood as able to take a different shape when pressure is applied on it.

It is the overall multilayered casing which is to be deformable and waterproof. However, it can comprise at least one non-waterproof layer, or partial layer, which allow fluid circulation inside the casing. Similarly, it can comprise non deformable parts which can constitute a backbone of the casing and orient its overall deformation. Preferably, it comprises an internal flexible layer which makes the device waterproof and an external, thicker layer which gives the casing its shape and overall mechanical properties.

The partition membrane defines the inner cavity and bears the vertical walls which define compartments. The partition membrane has a lower part and an upper part. Vertical is to be understood as linking these two parts or arising from any of these two parts, but a wall does not need to be parallel to the vertical axis to be considered a vertical wall. It can indeed present an angle with respect to the vertical axis, which can be variable depending on the portion of the wall.

The overall device typically presents a depth along the antero-posterior axis of the bearer. In certain embodiments, the depth is between 20 and 36 mm. In certain embodiments, the width is between 24 and 40 mm. In certain embodiments, the height is between 8 and 14 mm. In certain embodiments, the height is between 8 and 12 mm.

These dimensions need not be constant on the entire prosthesis. Although the device is called an intervertebral disc prosthesis, it does not have the shape of an exact disc. The term disc is used in reference to the anatomic structure the prosthesis is meant to replace. For instance, the device is preferably provided with low height zones and higher height zones which allow to control the overall fluid circulation and pressure response.

A compartment is defined by a zone in which the fluid contained in the inner cavity can circulate without mechanical impairment. When the walls do not present any orifice, or when the orifice/pores are small enough, it is easy to define the compartments. However, when the orifices grow larger, especially when their size takes all the height of the cavity, thus defining a complete interruption in the vertical wall, compartments definition can become trickier. It is also true in case of vertical walls which do not link the upper and lower parts together, which can also be referred to as "half-walls", or in case of vertical walls which end mid-way without completely closing a chamber.

In certain embodiments, two zones between which the fluid contained in the inner cavity can circulate without going through any orifice or pore are to be considered as belonging to the same compartment. An orifice is a recess in a vertical wall which smallest dimension is inferior to the height of the inner cavity at its position. For instance, a hole in a vertical wall is an orifice. Similarly, the previously called half-walls which arise from the upper or lower part of the inner cavity without linking it to its counterpart do define an orifice corresponding to the part between the end of the wall and said counterpart, which smallest dimension is indeed inferior to the height of the cavity.

In certain embodiments, the orifices present the highest dimension comprised between 1 and 6 mm. In certain embodiments, all the orifices do not have the same size. Orifices can have a round or angular shape, e.g. selected from an oval shape, a trapezoidal shape, or a polygonal shape such as star shape.

A porous or microporous membrane can also be used with smaller pores with a greater density so as to present similar fluid circulation through the wall in a more homogeneous way.

The non-toxic saline solution must be a solution which would not be harmful in case of accidental leakage of the prosthesis. In certain embodiments, the non-toxic saline solution is physiological serum. The solution can be completely liquid or can be dispersed into a hydrogel. It can also comprise additive, either for conservation or to fine tune its mechanical properties. For instance, it can comprise compounds which increase its viscosity.

Heterogeneous application of pressure is to be understood as an amount of applied pressure which is not the same on all the parts of the prosthesis.

Values of 0.05 and 3 MPa applied during between 10 seconds and 60 minutes correspond to standard pressure to which a disc is exposed in physiological conditions.

Reverting back to its native compartment upon removal of said pressure in a duration comprised between 10 seconds and 180 minutes correspond to a suitable kinetic allowing to mimic a regular intervertebral disc with the support of the remaining healthy vertebral column.

In certain embodiments, the external waterproof deformable casing comprises four layers. In order to maintain the shape, at least one of the layers can be structured in two different directions. In certain embodiments, the most external layer is a thick and solid layer, the most internal layer is flexible and waterproof, and the two intermediate layers are used as a radial backbone.

In certain embodiments, the walls are anchored into the most external layer of the external waterproof deformable casing, which allows to stabilize the walls and to prevent them to drift upon deformation.

In certain embodiments, the device comprises a number of walls in the antero-posterior plane comprised between 1 and 8.

In certain embodiments, the device comprises a number of walls in frontal plane comprised between 1 and 8.

In an advantageous embodiment, the inner cavity comprises pressure sensors. The sensors can allow monitoring the pressure and detect defect in the prosthesis. In certain embodiments, the sensors can communicate with an external device wirelessly.

The most external layer of the external waterproof deformable casing is reinforced with a rigid material. In certain embodiments, the rigid material is selected from polyester and polyethylene, used separately or in combination. Such materials allow for optimal and tunable mechanical properties whilst presenting good biocompatibility.

In certain embodiments, the vertical walls comprise at least one vertical wall presenting a multiply folded shape conferring spring-like properties. Such properties allow a higher response to pressure deformation and quicker return to its native shape upon deformation.

In certain embodiments, at least one vertical wall presents a tubular shape, which can trap part of the liquid so as to restrain its circulation and further tune the mechanical properties of the prosthesis upon deformation.

In certain embodiments, the water density in the inner cavity is constant.

In certain embodiments, the vertical walls comprise orifices with a larger dimension between 1 mm and 6 mm.

In certain embodiments, the external waterproof deformable casing is made of a 3D printable material.

In certain embodiments, the vertical walls are made of the same material than the peripheral partition membrane. The vertical walls and the peripheral partition membrane can be molded or made of a single piece, to provide optimal waterproof properties.

In certain embodiments, the intervertebral disk prosthesis comprises sensors able to measure parameters of the intervertebral disk prothesis and wirelessly communicate the measured value to an external device, wherein said parameters are preferably selected from pressure, pH, and salinity. Such measurements can allow detection of leakage or damages inside the prosthesis so as to decide proactively whether there is a need to replace the prosthesis or not.

Another object of the present disclosure is a disposable syringe for filling an intervertebral disk prothesis according to the present disclosure, comprising an external chamber configured to contain the non-toxic saline solution, and an internal chamber configured to receive a pressure sensor able to measure the pressure inside the inner cavity during its filling. Indeed, the prosthesis can be positioned empty or full, depending on the location. When the prosthesis needs to be filled in situ, it is of utmost importance to have very accurate control of the process, in particular the pressure inside the inner cavity so as to avoid overfilling or underfilling of the cavity.

It is thus another object of the present disclosure to provide a method for filling an intervertebral disk prothesis according to the disclosure, characterized in that it comprises the step of measuring the pressure during the filling of the intervertebral disk prothesis.

Another object of the disclosure is a method for positioning an intervertebral disk prothesis according to the disclosure between two cervical vertebrae wherein the intervertebral disk prothesis is filled with the non-toxic saline solution before being positioned between the two vertebrae. This is advantageous in case of a positioning between cervical vertebrae as they are of easier access than the lower vertebrae.

Another object of the present disclosure relates to a method for positioning an intervertebral disk prothesis according to the disclosure between two lumbar vertebrae wherein the intervertebral disk prothesis is filled with the non-toxic saline solution after being positioned between the two vertebrae. Indeed, since these vertebrae are not easily accessible, positioning the prothesis before filling it can be done with a cannula thus avoiding costly and hazardous belly surgery.

A probe is preferably used to monitor the pressure during the positioning of the prothesis according to the disclosure.

The probe is preferably left in place at the end of the positioning as its retreat can be hazardous and as it could prove useful in case a further intervention is needed.

The disclosure also relates to a medical treatment consisting in replacing a defective intervertebral disk of a patient with a intervertebral disk prothesis according to the present disclosure, wherein the maximum pressure applied on the disk without lifting any charge is calculated based on the weight and height of the patient and the dimensions of the orifices are configured to induce the saline solution to flow from one cavity compartment toward another upon heterogeneous application of said calculated pressure in a duration comprised between 10 seconds and 60 minutes, and to revert back to its native compartment upon removal of said pressure in a duration comprised between 10 seconds and 180 minutes.

The present disclosure shall be better understood based on the following detailed description of a non-limiting embodiment of the present disclosure, and on the annexed drawing on which:

Figure 1:
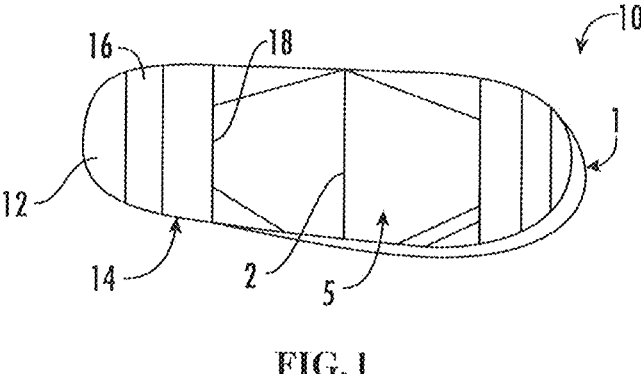
FIG. 1 is a across sectional view of a device according to the disclosure.

For clarity, the relative sizes and proportions of the elements depicted on the drawing have not always been respected, it is understood that the depicted views are merely schematic.

In an exemplary embodiment, it is provided a prosthesis with an injectable balloon presenting an external waterproof membrane 1. The membrane 1 is enclosed in a non-illustrated four layered casing.

Said casing is made of woven polyester which reproduces the annular circulation of the disc and is coated with a biological adhesive layer which allows proper adhesion to the articular tissues.

Figure 2:
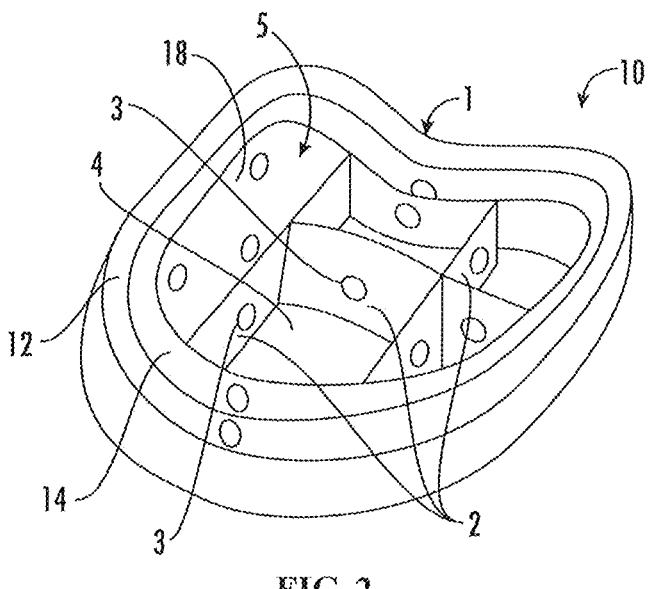
FIG. 2 is a perspective view of a device according to the disclosure without the upper part of the partition membrane.

As shown in FIGS. 1 and 2, an intervertebral disc 10 comprises an outer casing or waterproof membrane 1 that defines an internal cavity filled with physiological serum. The waterproof membrane presents a lower surface 4 and an upper part surface which is not illustrated. In certain embodiments, membrane 1 comprises an outer layer 12 and an inner layer 14. In some embodiments, membrane further comprise an intermediate layer 16 (see FIG. 1). Inner layer 14 may comprise an internal membrane with an inner wall 18 that delimits an inner cavity. The inner cavity includes a number of vertical walls 2 that define a plurality of compartments 5. The vertical walls 2 are distributed asymmetrically in the inner cavity so that a posterior part of the inner cavity comprises fewer and/or larger cavity compartments than an anterior part of the inner cavity.

As opposed to existing prosthesis which are filled with silicone, physiological serum is harmless in case of leakage. In order to get a proper rheology, circulation of the physiological serum is hampered and organized by internal walls 2. Some of these walls are vertical while others are of horizontal orientation as depicted on FIGS. 1 and 2, thus defining a plurality of compartments, such as compartment 5.

Walls present oval apertures 3 which allow fluid circulation between the compartments.

The casing and the partition membrane are 3D printed based on imaging data of the patient, allowing for a personalized prosthesis. The casing and the membrane are thus made of materials which are both biocompatible and 3D printable, such as polyethylene, silicone or polyurethane.

The pressure inside the prosthesis must not exceed the pressure of a disc, i.e. comprised between 200 and 300 kPa, which is made possible by the fact that the fluid used is physiological serum, as opposed to silicone in prior art. The pressure inside the disc is thus controlled during its filling by appropriate material. Advantageously, pressure sensors able to communicate wirelessly with an external device are used to monitor the pressure at all times.

The prosthesis is positioned empty through a cannula and then filled in situ through a valve, which allows to avoid belly surgery.

For cervical prosthesis however, it is possible to position a prefilled prosthesis as there is no such constraints.

The filling speed, the volume and the target pressure are preestablished based on the size of the prosthesis and of the weight of the patient. The shape of the filled disc is designed to be a substitute to the normal disc but ideally also spreads on the vertebrae in a bean shape with rounded vertical faces.

Walls 2 are oriented so as to maintain the disc in place. Indeed, the pressure applied to the envelope could cause a rolling effect which must be avoided. The disc must also be able to resist the shearing stress applied laterally, rotationally, and along the anteroposterior axis.

The prosthesis according to the present embodiment deforms upon compression and returns to its original shape when the pressure is released. The return operates between 5 and 10 minutes.

In order to mimic the mechanics of a natural intervertebral disc, the walls and the apertures are configured to ease the fluid circulation toward the front: there are less walls and more opening in the front part of the prosthesis to favor a laterally triangular compression.

The walls 2 and the openings 3 are positioned depending on the biomechanical dynamics of the site where the prosthesis is to be positioned, and depending on the weight of the patient. The walls can be continuously linked to the partition membrane 1 or can present loose parts.

The fibers of the walls 2 can be either vertical, horizontal or oblique and their density, orientation and structure can either be constant or vary depending on their application potential.

The internal walls are configured to allow the full circulation of the fluid and do not act as dialysis membrane.

The positioning of the prosthesis according to the present embodiment is done to replace an intervertebral disc after exeresis of disc tissue with instrumentation for height adjustment, trial template using an inflatable balloon of the same shape, and centering and positioning control using radiopaque markers.

In an alternative embodiment, the prosthesis according to the present disclosure can be inserted intra-articularly in intervertebral discs, posterior vertebral joints such as facet joints or zygapophyses, shoulder, elbow, wrist, hip, knee, ankle, talus and any other joint location of the locomotor system.

The disclosure is not limited to the described embodiments. Unless stated otherwise, the expression "comprising one" is to be understood as "comprising at least one" and "or" is to be understood as "and/or".

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments, but should be defined only in accordance with the following claims and their equivalents.

The invention claimed is:

1. Intervertebral disk prosthesis comprising an external multilayered casing surrounding an internal membrane delimiting an outer space and an inner cavity,
  wherein the multilayered casing comprises four layers, the four layers including an external most layer reinforced with a rigid material, two intermediate layers as a radial backbone, and a flexible and waterproof innermost layer,
  wherein the inner cavity is partitioned by vertical walls delimiting at least four cavity compartments configured to be filled with a non-toxic saline solution,
  wherein the vertical walls comprise porous membranes configured to induce the saline solution to flow from one cavity compartment toward another upon heterogeneous application of a pressure comprised between 0.05 and 3 MPa in a duration comprised between 10 seconds and 60 minutes, and to revert back to its native compartment upon removal of said pressure in a duration comprised between 10 seconds and 180 minutes,
  wherein the vertical walls are distributed asymmetrically in the inner cavity so that a posterior part of the inner cavity comprises larger cavity compartments than an anterior part of the inner cavity, and
  wherein the vertical walls are anchored into the external most layer of the multilayered casing.

2. Intervertebral disk prothesis according to claim 1, wherein the inner cavity comprises pressure sensors.

3. Intervertebral disk prothesis according to claim 1, wherein the vertical walls comprise at least one vertical wall presenting a tubular shape.

4. Intervertebral disk prothesis according to claim 1, wherein a density of the non-toxic saline solution in the inner cavity is constant.

5. Intervertebral disk prothesis according to claim 1, wherein the vertical walls comprise orifices with a dimension between 1 mm and 6 mm.

6. Intervertebral disk prothesis according to claim 1, wherein the external casing is made of a 3D printable material.

7. Intervertebral disk prothesis according to claim 1, wherein the vertical walls are made of the same material as the internal membrane.

8. Intervertebral disk prothesis according to any claim 1, wherein the non-toxic saline solution is physiological serum.

9. Intervertebral disk prothesis according to claim 1, further comprising sensors configured to measure parameters of the intervertebral disk prothesis and wirelessly communicate the parameters to an external device, wherein said parameters are selected from a group consisting of pressure, pH, and salinity.

10. Intervertebral disk prosthesis of claim 1, wherein the rigid material includes polyester, polyethylene, or a mixture thereof.

11. Method for filling an intervertebral disk prothesis according to claim 1, wherein it comprises the step of measuring the pressure during the filling of the intervertebral disk prothesis.

12. Method for positioning an intervertebral disk prothesis according to claim 1 between two cervical vertebrae wherein the intervertebral disk prothesis is filled with the non-toxic saline solution before being positioned between the two vertebrae.

13. Method for positioning an intervertebral disk prothesis according to claim 1 between two lumbar vertebrae wherein the intervertebral disk prothesis is filled with the non-toxic saline solution after being positioned between the two vertebrae.

14. Method for positioning an intervertebral disk prothesis according to claim 1 between two vertebrae wherein a probe is used to monitor the pressure during the positioning of the intervertebral disk prosthesis.

15. Method for positioning an intervertebral disk prothesis according to claim 14, wherein the probe is left in place at the end of the positioning.

16. Medical treatment comprising replacing a defective intervertebral disk of a patient with a intervertebral disk prothesis according to claim 1, wherein the maximum pressure applied on the defective intervertebral disk without lifting any charge is calculated based on the weight and height of the patient and the dimensions of orifices defined in the vertical walls are configured to induce the saline solution to flow from one cavity compartment toward another upon heterogeneous application of said calculated pressure in a duration comprised between 10 seconds and 60 minutes, and to revert back to its native compartment upon removal of said pressure in a duration comprised between 10 seconds and 180 minutes.

* * * * *